United States Patent [19]
Wallner et al.

[11] Patent Number: 5,124,935
[45] Date of Patent: Jun. 23, 1992

[54] GEMSTONE IDENTIFICATION, TRACKING AND RECOVERY SYSTEM

[75] Inventors: Hermann F. Wallner; Dana J. Vanier, both of Ottawa, Canada

[73] Assignee: Omphalos Recovery Systems Inc., Toronto, Canada

[21] Appl. No.: 620,477

[22] Filed: Nov. 30, 1990

[51] Int. Cl.⁵ .......................................... G01N 21/00
[52] U.S. Cl. ...................................... 364/525; 356/30
[58] Field of Search .................. 364/525, 409, 571.01; 358/261, 8; 356/30, 31

[56] References Cited

U.S. PATENT DOCUMENTS

| | | | |
|---|---|---|---|
| 3,947,120 | 3/1976 | Bar-Isaac et al. | 356/30 |
| 4,749,847 | 7/1988 | Despres | 235/487 |
| 4,893,840 | 1/1990 | Berkowitz | 283/81 |
| 4,951,825 | 8/1990 | Hawkins et al. | 209/558 |

FOREIGN PATENT DOCUMENTS

| | | |
|---|---|---|
| 0156545 | 9/1982 | Japan . |
| 0158544 | 9/1982 | Japan . |
| 2215041 | 9/1989 | United Kingdom . |

*Primary Examiner*—Parshotam S. Lall
*Assistant Examiner*—S. A. Melnick

[57] ABSTRACT

A system for the effective recording and recovery of gemstones uses site machines for recording the optical response of gemstones with these optical responses being forwarded to a central database for classifying in a manner to allow effective searching of the database. The site machine progressively scans the optical response of the gemstone and provides an accurate record of the optical response of the gemstone. Gemstones reported to the central database as being stolen have their records duplicated in a separate database which can be searched remotely by police and other enforcement agencies for a possible match with the optical response of gemstones they have recovered.

17 Claims, 2 Drawing Sheets

GEMSTONE IDENTIFICATION, TRACKING AND RECOVERY SYSTEM

FIELD OF THE INVENTION

The present invention relates to a system for classifying and recording information with respect to gemstones whereby the gemstones may be accurately identified and in a manner to produce a database whereby recovered stolen or missing gemstones may be compared with the database for accurate identification.

BACKGROUND OF THE INVENTION

A number of systems have been proposed for classifying and identifying gemstones to provide what may be referred to as an optical fingerprint of the gemstone. The optical fingerprint is accurate and acceptable by the courts for determining whether a gemstone under consideration is the same gemstone which produced a previously recorded fingerprint.

In theft of gemstones, the most common problem is being able to accurately identify a stolen gemstone as being a particular gemstone which was stolen from a certain owner. This problem is of particular concern to insurance companies, in that gems are often insured and it has been difficult to identify the stolen gemstone even if it is recovered. Insurance companies in the past have also been subject to fraudulent claims. Thus, identification of gemstones and the tracking of gemstones remains a problem.

U.S. Pat. No. 3,947,120 discloses a particular arrangement for providing an optical fingerprint of a gemstone where a laser beam is focused on a gemstone and the optical response of the gemstone is recorded on a recording medium, preferably a photographic medium. This arrangement provides a fingerprint of the gemstone which is reproducible and has been held by the courts to be sufficient evidence to prove that the gemstone under consideration having a certain optical response is the same as a previously identified gemstone having essentially the same optical response.

Although this patent discloses a particular method for fingerprinting of gemstones, there remains a very significant problem of being able to actually use this information for identification of gemstones which may be known as missing or stolen.

SUMMARY OF THE INVENTION

The present invention provides a system for improved recording of gemstone fingerprints and a method of collecting these recorded fingerprints, classifying of the fingerprints whereby a database is developed which can be effectively searched.

The present invention is also directed to a recovery system whereby gemstones recovered by police or other authorities can be remotely scanned using this technology with the resulting optical response compared to other optical responses on the database for proper identification of the gemstone and a matching with a particular gemstone record, if indeed the stolen gemstone has previously been recorded.

The present invention can have a significant impact with respect to the tracking of gemstones and may also make it substantially more difficult to trade stolen gemstones.

A device for producing a reproducible identification pattern of a polished gemstone according to the present invention comprises light directing means for directing a focused beam of light onto a gemstone orientated in a particular known manner to produce an output of the internal refraction and reflection characteristics of the gemstone and means for recording of a selected portion of the output in a manner to record the relative size and location of the reflected light beams and wherein the recording means automatically adjusts for variations in the intensity of different light beams such that variations in intensity are adjusted for thereby increasing the accuracy of the size measurement.

According to an aspect of the invention, the device for producing reproducible identification pattern of a polished gemstone comprises means for directing a focused beam of light onto a gemstone orientated in a particular known manner to produce an optical response of the internal refraction and reflection characteristics of the gemstone, and means for assessing the relative size and location of a selected portion of the output of the reflected light beams and wherein the means for assessing optically scans the selected portion to produce an electronic record of the optical response of the gemstone.

A system for recording of gemstones, according to the present invention, comprises a central recording means for electronically receiving and recording optical assessment of gemstones, a plurality of optical assessment stations which optically assess gemstones by causing said gemstones to produce an optical response based upon the individual recognizable characteristics of the gemstone and producing an electronic signal of the optical response of the gemstone and forwarding the optical response of the gemstone to the central recording means for electronically receiving and recording optical assessments of gemstones.

A gemstone recovery identification system, according to the present invention, comprises a gemstone database of classified gemstones classified by means of optical response characteristics of the gemstones, characteristics of the gemstones and the owner of the gemstone in a format that is capable of being efficiently searched electronically with the system including means for receiving and classifying the optical response of a gemstone which has been recovered, but requires identification, and electronically searching the gemstone database for a match between one of the classified gemstones and the classified optical response of the recovered gemstone.

BRIEF DESCRIPTION OF THE DRAWINGS

Preferred embodiments of the invention are shown in the, drawings, wherein.

DETAILED DESCRIPTION OF THE PREFERRED EMBODIMENTS

Figure 1:
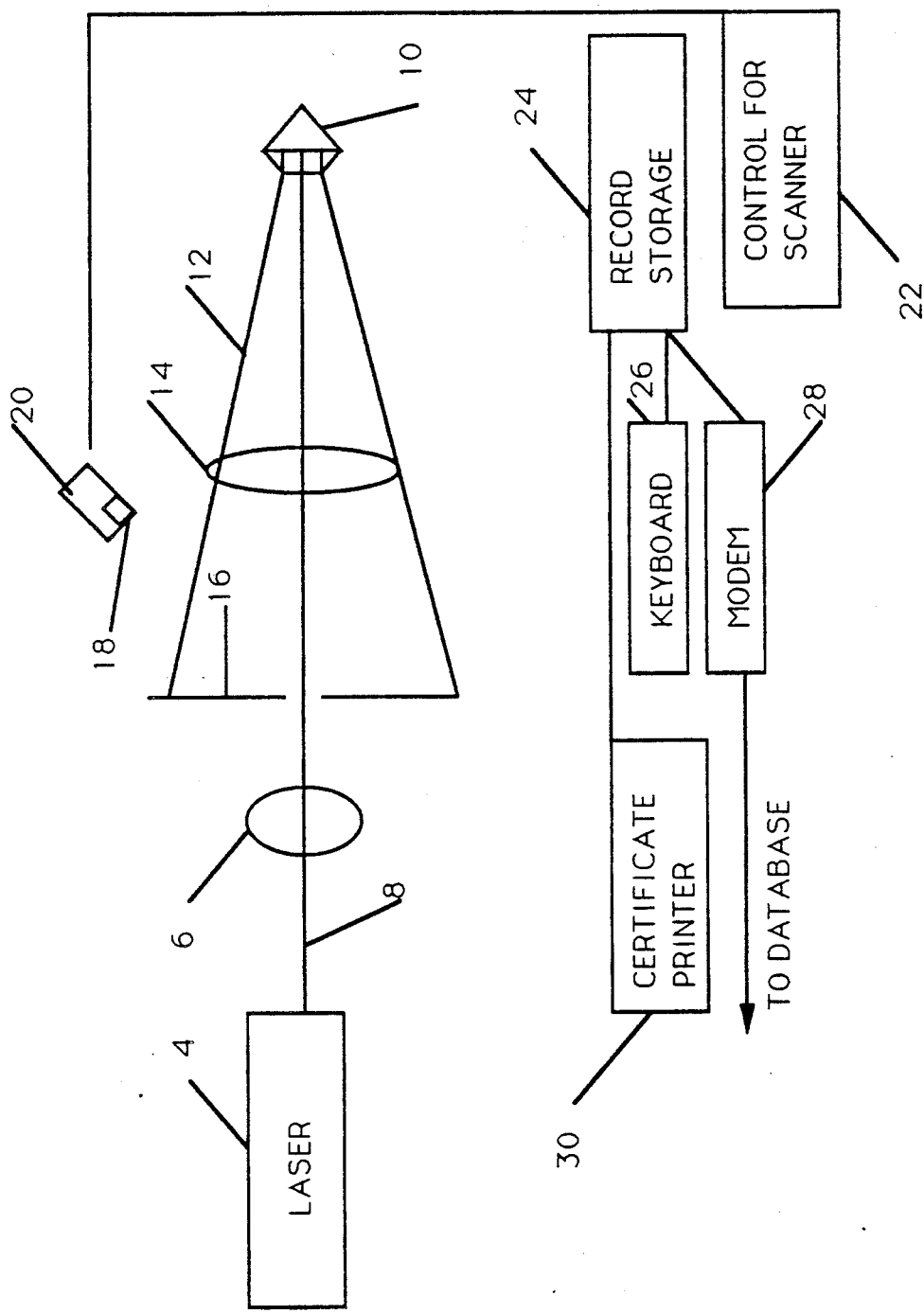
FIG. 1 is a schematic of the scanning machine of the present invention.

The scanning machine generally shown as 2 in Figure includes a laser 4 for producing a laser beam 8 which is projected at the gemstone 10. Laser beam 8 passes through a first focusing lens 6, passes through a central hole in the display screen 16 and passes through a second focusing lens 14 before striking the gemstone 10. The laser beam striking the gemstone 10 which is held in a particular manner, as generally shown and described in U.S. Pat. No. 3,947,120, produces an optical response 12 which is focused by the second focusing lens 14 onto the display screen 16. A scanner 18 is positioned to one side of the scanning machine out of the direct light transmitting region of the optical response displayed on display screen 16, with the scanner viewing only a selected linear segment of the display screen 16. A track arrangement 20 progressively moves the scanner across the display screen to provide a complete optical record of the optical response shown on the display screen. This controlled movement of the scanner along track 20 is controlled by controller 22. The output from the scanner 18 is recorded in the record storage arrangement 24. Thus, it can be appreciated that a complete record is stored in record storage 24 of the optical response 12 produced by a particular gemstone 10.

The scanner is a charged coupled device which can accurately receive the signal from a particular segment of the display screen 16. By mechanically moving the scanner across the display screen along track 20, a complete assessment of the optical response is compiled. This mechanical moving of the scanner 18 greatly reduces the cost of the scanner, whereas a scanner which would view the entire screen would be many times more expensive and thus would render the site machine excessively expensive for the average jeweler to maintain within his own premises. The jeweler who would have this machine in his shop upon selling of the gemstone would key in particular information with respect to the owner of the gemstone, the address, the particular cut, color, weight and other characteristics of the gemstone which he can accurately determine, and combine this information with the optical response of the particular gemstone. A modem 28 is provided for sending of the record storage 24 to a central database 40 shown in FIG. 2 where the optical response will subsequently be classified in a manner that it may be accurately searched. Associated with the scanning machine 2 is a certificate printer 30 which will provide a hard copy of the optical response 12 of the particular gemstone as well as providing the other information entered at the keyboard. The scanner 18 includes means for automatically adjusting for different light intensities as it scans a particular segment. The purpose of the scanner is to accurately determine the size and location of the individual beams that are found in the optical response. This is contrast to a photographic record where the intensity of these beams is inherently recorded on the photographic material and can inaccurately influence the size of the beam due to the effect of a very high or low intensity. Therefore, the scanner 18 automatically adjusts for variations in the intensity of the different light beams to provide a more accurate assessment of the size and location of the light beams produced in the optical response 12. The progressive scanning of the optical response lends itself to this correction for intensity. It can be appreciated that a scanner capable of reading the entire screen is also possible and can adjust for varying intensity.

Preferably, the record storage 24 includes data compression capability as the optical record is particularly appropriate for data compression as the size and location of the hot spots are of prime importance. Data compression can take many forms including run length encoding.

Figure 2:
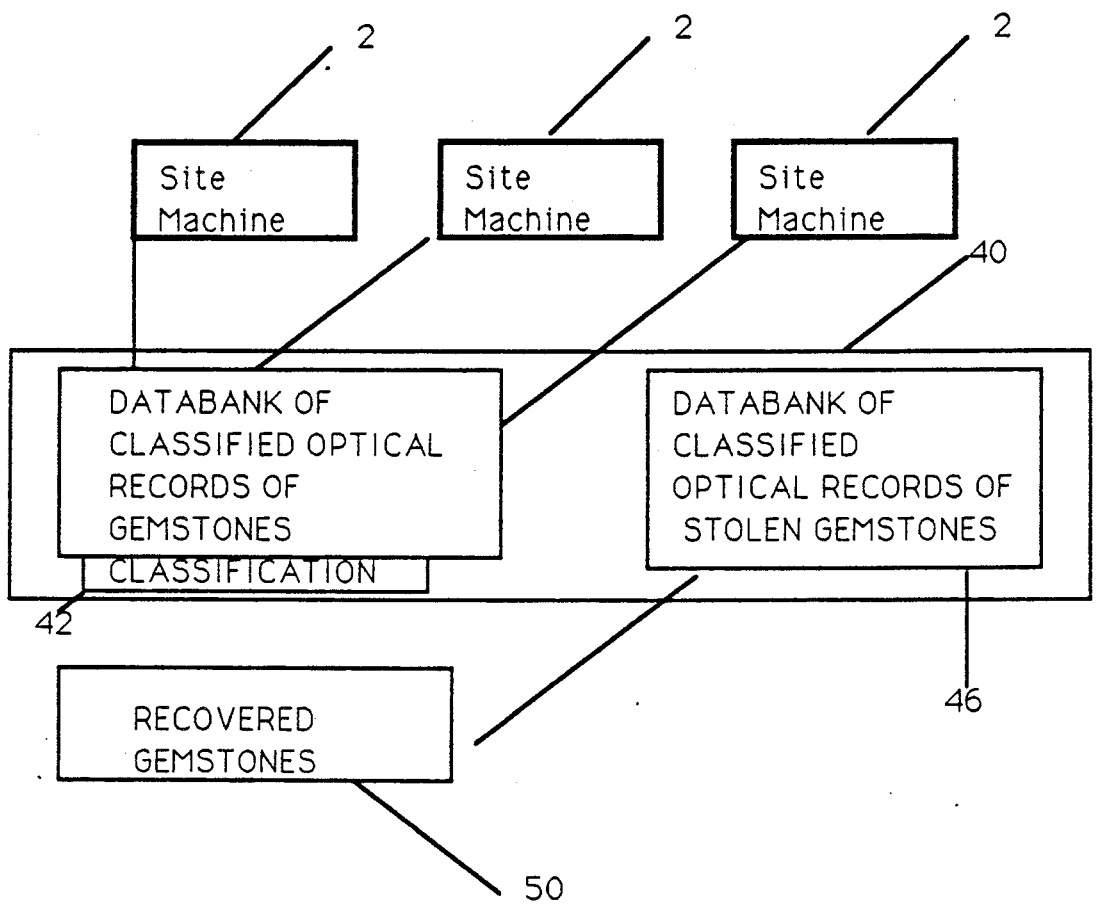
FIG. 2 is a schematic of the overall gemstone recording and recovery system.

The overall system is generally shown in FIG. 2 and comprises a central database 40 which includes a classification section 42 and a databank 44 of classified gemstones. This databank 44 has associated therewith a sub group 46 of gemstones indicated as being stolen or missing by the particular insurance company or the owner.

Recovered gemstones are optically scanned by a particular site machine at a police station, such as 50, and the optical response of these gemstones are compared with the sub group 46 of the gemstones stolen or missing as identified by the particular owners. In this way, police departments in far varying jurisdictions can compare the gemstones recovered from thieves or suspected of being stolen with a database of gemstones which have previously been identified as being stolen or missing.

The classification of the gemstones carried out at in FIG. 2 relies on a polar coordinate system for identifying the largest area light beams of the optical response identified as large circles on the hard copy of the optical response. The largest area light beam is identified as a number 1 light beam and the remaining light beams are progressively identified by size. The largest light beam is considered to be at a zero angle and all other light beams are plotted relative to this major light beam. The distance from the center point is also measured to provide an accurate location identification.

This particular classification arrangement renders it quite convenient to search, as the optical response of the suspected stolen gemstone is classified and the various light beams thereof are again plotted in this manner. Software accurately compares this response with known responses based upon the particular angles of the light beams and then varying of the particular light beams which are considered the dominant light beams. This can be carried out in software and is very efficient and may result in several searches or several permutations of the actual optical response. After a number of possible matches have been identified, then further comparison can be made with respect to the distance from the center as well as the much more detailed response characteristics. Based upon a comparison of the recorded optical responses, the expert can then provide his opinion whether it is an identical match or not.

As can be appreciated, the system operates most efficiently if jewelers throughout the country or throughout the territory all have these individual site machines and upon the sale of a gemstone, make an accurate optical fingerprint of the gemstone using the site machine to evaluate the gemstone. This record is then recorded in a central databank of gemstones and is preferably forwarded electronically to the databank. Compression of the optical response characteristics of a particular gemstone can be accomplished using standard techniques. The actual recording is preferably based on the size and location of these light spots resulting from the particular light beams produced in the optical response. Run length encoding is particularly suitable for compression of this data.

Although various preferred embodiments of the present invention have been described herein in detail, it will be appreciated by those skilled in the art, that variations may be made thereto without departing from the spirit of the invention or the scope of the appended claims.

The embodiments of the invention in which an exclusive property or privilege is claimed are defined as follows:

1. A device for producing a reproducible identification pattern of a polished gemstone comprising light directing means for directing a focused beam of light onto a gemstone orientated in a particular known manner to produce an output of the internal refraction and reflection characteristics of the gemstone including reflected light beams having particular locations, sizes and intensities, and means for recording the output in a manner to record the relative size and location of the reflected light beams, and wherein said recording means progressively scans the output and automatically adjusts for variations in their intensity of different light beams during the scanning of the output.

2. A device as claimed in claim 1 wherein said recording means includes means for applying data compression techniques to the output of the reflected light beams.

3. A device for producing a reproducible identification pattern of a polished gemstone comprising means for directing a focused beam of light onto a gemstone orientated in a particular known manner to produce an optical response of the internal refraction and reflection characteristics of the gemstone including reflected light beams having particular locations, sizes and intensities, and means for assessing the relative size and location of a selected portion of the output of reflected light beams, and wherein said means for assessing optically scans said optical response and makes adjustments throughout the scanning process to accommodate changes in intensity of the light beams within the optical response and produces an electronic record of the optical response of said gemstone from which relative size and location of the internal refraction and reflection characteristics of the gemstone are known and includes means for transmitting said electronic record to a remote computer.

4. A device as claimed in claim 3 wherein said means for assessing optically scans segments of said optical response which segments collectively represent said optical response of said gemstone.

5. A system for recording of gemstones comprising a central recording means for electronically receiving and recording optical assessments of gemstones, a plurality of optical assessment stations which optically assess gemstones by causing said gemstones to produce an optical response based upon the individual recognizable characteristics of the gemstone which recognizable characteristics include reflected light beams defining areas of high illumination and different sizes, and means for producing an electronic signal of the optical response of said gemstone and forwarding the optical response of said gemstone to said central recording means for electronically receiving and recording optical assessments of gemstones, said central recording means upon receipt of a gemstone optical response for recording classifies said optical response in a manner allow accurate comparison of a given optical response with optical responses classified and recorded at said central recording means by classifying according to the size of areas of high illumination and assigning polar coordinates to the areas of high illumination.

6. A system as calimed in claim 5 including means for applying data compression techniques to produced optical responses of emstones which forms part of said means for producing an electronic signal.

7. A gemstone recovery identification system comprising a gemstone database of classified gemstones classified by means of optical response characteristics of the gemstones including the size and particular locations of light beams of the particular optical response characteristics, characteristics of the gemstone and owner of the gemstone in a format that is capable of being efficiently searched electronically, the characteristics of the gemstones being classified by a device which produces reproducible identification patterns for respective polished gemstones, said device comprising light directing means for directing a focused beam of light onto a gemstone orientated in a particular known manner to produce an output of the internal refraction and reflection characteristics of the gemstone, and means for recording of the output in a manner to record the relative size and location of the reflected light beams, and wherein said recording means progressively scans the output and automatically adjusts for variations in the intensity of different light beams during the scanning of the output; said gemstone recovery identification system further including means for receiving the digitized optical response of a gemstone which has been recovered but requires identification and electronically searching the gemstone database for a match between one of the classified gemstones and said digitized optical response of said recovered gemstone.

8. A gemstone recovery identification system as claimed in claim 7 wherein said gemstone database of classified gemstones is divided into a separate group of gemstones which have been identified as being stolen or missing, and wherein the digitized optical response of said recovered gemstone is compared to said separate group of stolen or missing gemstones.

9. A method for producing a reproducible identification pattern of a polished gemstone comprising directing a focused beam of light onto a gemstone orientated in a particular known manner to produce an output of the internal refraction and reflection characteristics of the gemstone made up of reflected light beams having particular locations, sizes and intensities, and recording the output in a manner to record the relative size and location of the reflected light beams and adjusting the recording as a function of the light intensity of different reflected light beams during the recording of the output.

10. A method as claimed in claim 9 including transmitting the recorded selected portion to a remote database.

11. A method as claimed in claim 10 including applying data compression techniques prior to transmitting the recorded selected portion to a remote database.

12. A method for recording of gemstones comprising a central recording means for electronically receiving and recording optical assessments of gemstones, a plurality of optical assessment stations for optically assessing gemstones by producing an optical response based upon the individual recognizable characteristics of the gemstone by focusing a laser on the gemstone, projecting the reflected image or pattern and refracted light onto a screen to produce an image or pattern and measuring the pattern by scanning the screen with a light sensitive arrangement; and producing an electronic signal of the optical response of said gemstone and forwarding the optical response of said gemstone to said central recording means for electronically receiving and recording optical assessments of gemstones and wherein the recording of the optical assessments of gemstones is by means of polar coordinates used to identify the particular locations of light beams of the optical response relative to other light beams of the optical response.

13. A method as claimed in claim 12 wherein said central recording means upon receipt of a gemstone optical response for recording classifies said optical response in a manner allow accurate comparison of a given optical response with optical responses classified and recorded at said central recording means.

14. A method as claimed in claim 13 wherein classification of the optical response includes classifying according to the relative size and location of areas of high illumination.

15. A method as claimed in claim 13 wherein classification of the optical response includes classifying according to the size of areas of high illumination and assigning polar coordinates to the areas of high illumination.

16. A method as claimed in claim 12 including applying data compression techniques to produced optical responses of gemstones.

17. A gemstone recovery identification method comprising forming a gemstone database of classified gemstones classified by means of optical response characteristics of the gemstones, characteristics of the gemstone and owner of the gemstone in a format that is capable of being efficiently searched electronically, and receiving the optical response of a gemstone which has been recovered but requires identification and electronically searching the gemstone database for a match between one of the classified gemstones and said optical response of said recovered gemstone and wherein the optical response of the characteristics of the gemstones includes light beams at particular locations and of particular sizes and the classification of the gemstones includes identification of the location and size of light beams of the optical response of the respective gemstones by means of polar coordinates.

* * * * *